(12) United States Patent
Dann et al.

(10) Patent No.: US 6,223,085 B1
(45) Date of Patent: *Apr. 24, 2001

(54) DEVICE AND METHOD FOR PREVENTING RESTENOSIS

(75) Inventors: Mitchell Dann, Jackson, WY (US); Scott P. Thome, Waite Park, MN (US); Jonathan R. McGrath, Chanhassen, MN (US); Eric N. Rudie, Maple Grove, MN (US); Jonathan L. Flachman, Minneapolis, MN (US); Teruo T. Hirose, Bronx, NY (US)

(73) Assignee: Urologix, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/852,154

(22) Filed: May 6, 1997

(51) Int. Cl.[7] .................................................. A61B 17/36
(52) U.S. Cl. ........................... 607/101; 606/29; 607/105; 607/156
(58) Field of Search ................... 606/27–31, 7–13, 606/17; 607/101, 102, 113, 116, 154–156

(56) References Cited

U.S. PATENT DOCUMENTS

| | | | |
|---|---|---|---|
| 2,799,273 | 7/1957 | Oddo | 128/325 |
| 4,311,154 | 1/1982 | Sterzer et al. | 128/804 |
| 4,632,127 | 12/1986 | Sterzer | 128/804 |
| 4,643,186 | 2/1987 | Rosen et al. | 128/303.1 |
| 4,662,383 | 5/1987 | Sogawa et al. | 128/784 |
| 4,709,698 | 12/1987 | Johnston et al. | 128/303.12 |
| 4,824,436 | 4/1989 | Wolinsky | 604/53 |
| 4,872,458 | 10/1989 | Kanehira et al. | 128/401 |
| 4,878,492 | 11/1989 | Sinofsky et al. | 128/303.1 |
| 4,924,863 | 5/1990 | Sterzer | 606/27 |
| 4,932,956 | 6/1990 | Reddy et al. | 606/192 |
| 4,932,958 | 6/1990 | Reddy et al. | 606/192 |
| 4,955,377 | 9/1990 | Lennox et al. | 128/401 |
| 4,998,933 | 3/1991 | Eggers et al. | 606/41 |
| 5,007,437 | 4/1991 | Sterzer | 428/786 |
| 5,019,075 | 5/1991 | Spears et al. | 606/7 |
| 5,057,106 * | 10/1991 | Kasevich et al. | 606/7 |
| 5,061,267 * | 10/1991 | Zeiher | 607/116 |
| 5,098,429 | 3/1992 | Sterzer | 606/28 |
| 5,150,717 * | 9/1992 | Rosen et al. | 606/27 |
| 5,151,100 | 9/1992 | Abele et al. | 606/28 |
| 5,226,430 * | 7/1993 | Spears et al. | 606/28 |
| 5,405,322 | 4/1995 | Lennox et al. | 604/53 |

(List continued on next page.)

*Primary Examiner*—Robert L. Nasser
(74) *Attorney, Agent, or Firm*—Kinney & Lange

(57) ABSTRACT

A method and apparatus for reducing restenosis of a stenotic region of a blood vessel after performing a dilatation angioplasty treatment is disclosed. The method includes radiating microwave energy from a microwave antenna to kill a medial tissue layer of the blood vessel in the stenotic region. The radiation is applied during or after inflation of dilatation balloon to permanently dilate the stenotic region. When radiation is applied during dilatation of the stenotic region, the dilatation balloon forms a seal against the inner wall surface of the blood vessel to exclude blood in the vessel from contacting the stenotic region. The method preferably further includes cooling the blood circulating in the blood vessel about a shaft of the catheter with cooling fluid circulating within cooling lumens of the catheter and cooling an inner wall surface of the blood vessel in the stenotic region during the application of radiation to the medial cell layer. Finally, the method also preferably includes perfusing blood in the vessel through the catheter across the stenotic region during dilatation of the stenotic region to maintain circulation of blood through the blood vessel during the dilatation of the stenotic region.

16 Claims, 7 Drawing Sheets

U.S. PATENT DOCUMENTS

| | | | | |
|---|---|---|---|---|
| 5,417,653 | * | 5/1995 | Sahota et al. | 606/7 |
| 5,456,661 | * | 10/1995 | Narcisco, Jr. | 606/15 |
| 5,470,352 | * | 11/1995 | Rappaport | 607/101 |
| 5,496,271 | | 3/1996 | Burton et al. | 604/54 |
| 5,496,311 | | 3/1996 | Abele et al. | 606/28 |
| 5,503,613 | | 4/1996 | Weinberger | 600/3 |
| 5,509,929 | * | 4/1996 | Hascoet et al. | 607/101 |
| 5,545,137 | * | 8/1996 | Rudie et al. | 607/101 |
| 5,607,419 | * | 3/1997 | Amplatz et al. | 606/7 |
| 5,775,338 | * | 7/1998 | Hastings | 606/27 |
| 5,957,917 | * | 10/1991 | Doiron et al. | 606/7 |

* cited by examiner

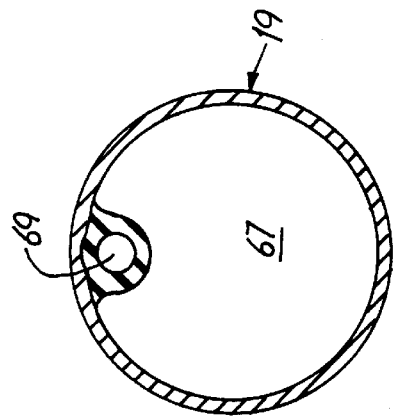
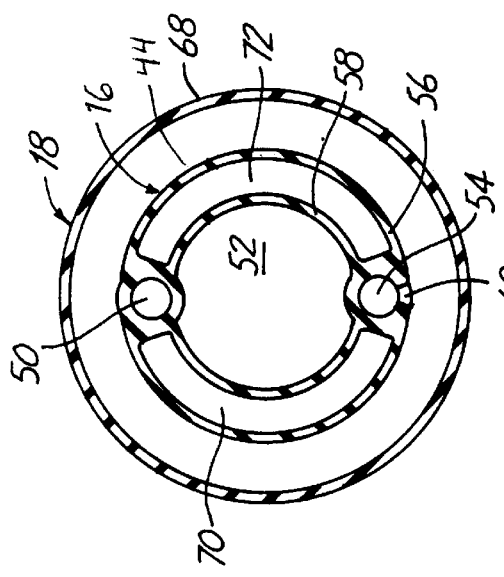
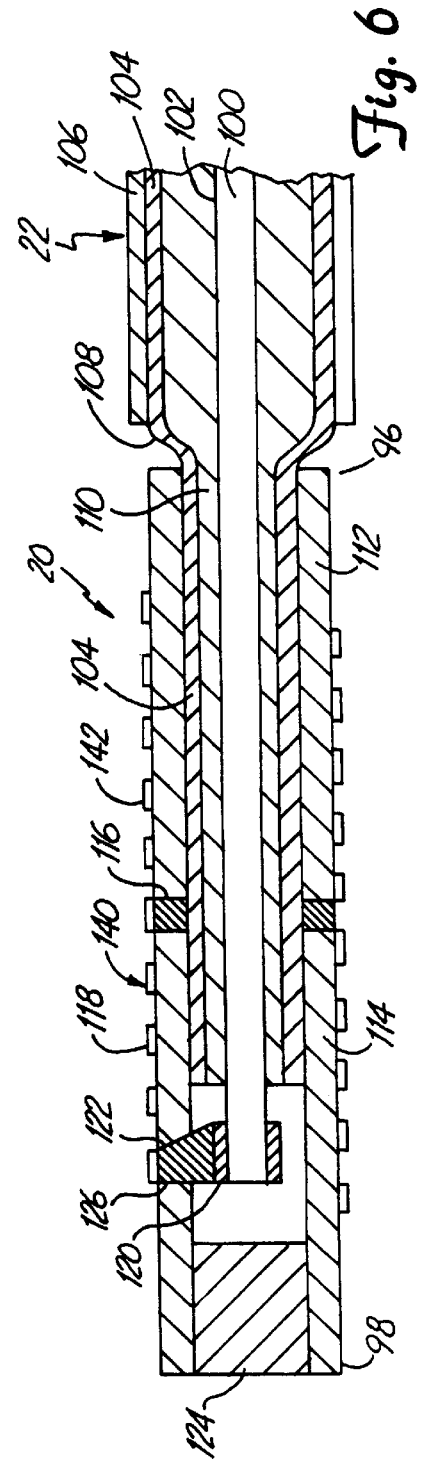

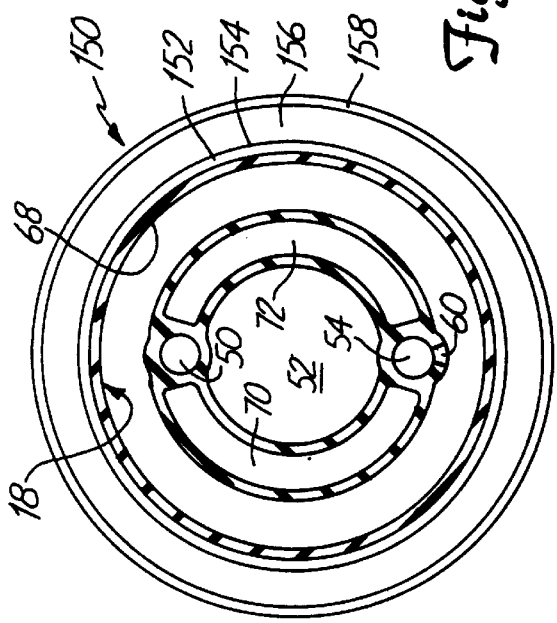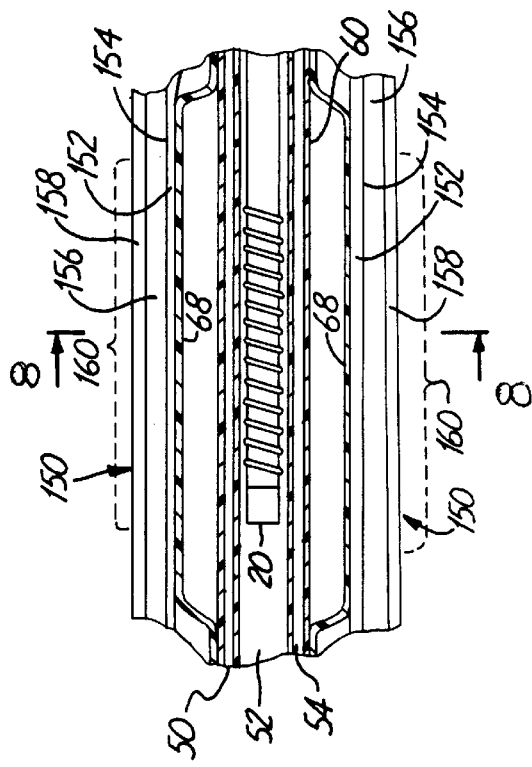

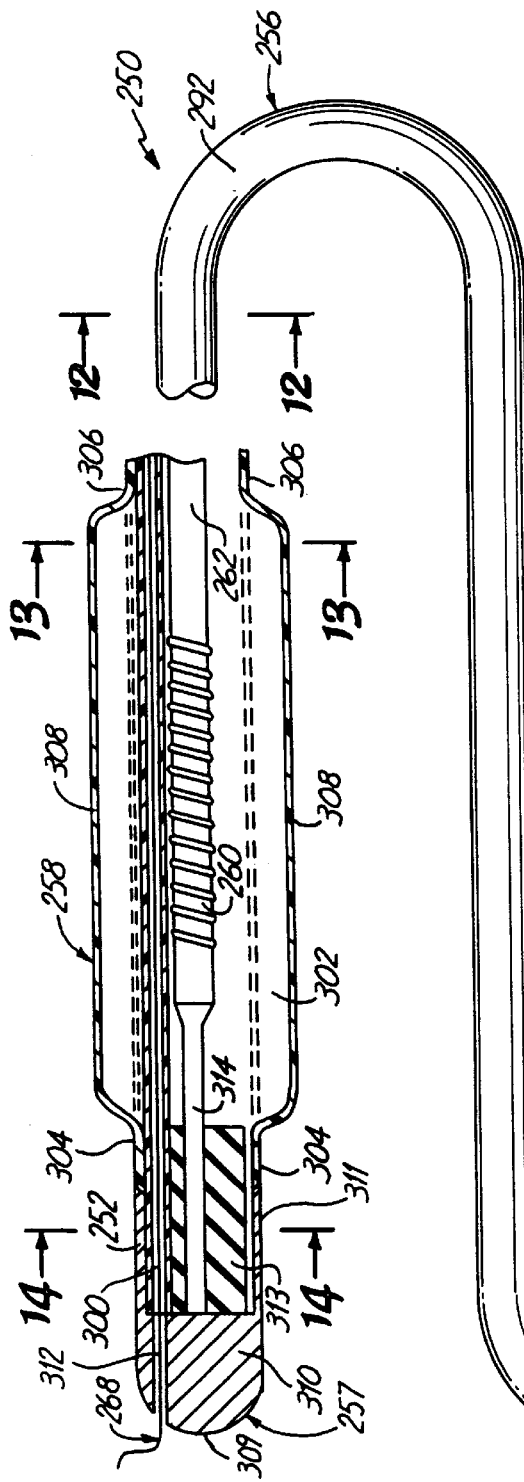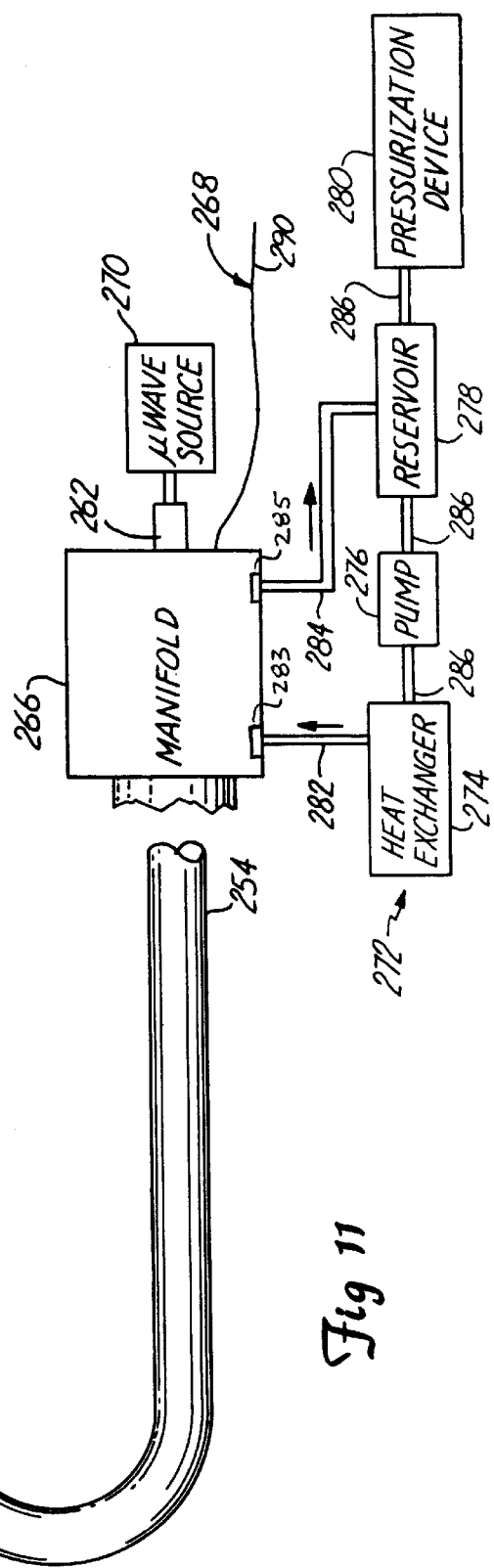
Fig 11

DEVICE AND METHOD FOR PREVENTING RESTENOSIS

REFERENCE TO CO-PENDING APPLICATIONS

Reference is hereby made to copending application Ser. No. 08/672,505, filed Jun. 17, 1996, titled MICROWAVE ANTENNA FOR ARTERIAL APPLICATOR and co-pending application Ser. No. 08/664,363 filed Jun. 17, 1996, titled ARTERIAL MICROWAVE APPLICATOR WITH COOLING.

BACKGROUND OF THE INVENTION

The present invention relates to treating blood vessels, and in particular, to preventing restenosis after an angioplasty dilatation treatment, or other controlled injury, of a stenotic region of a blood vessel.

Percutaneous transluminal coronary angioplasty (PTCA) is commonly used to treat an artery obstructed by a stenosis. In PTCA, a catheter having a balloon at its distal end is advanced through the cardiovascular system until the balloon lies across the stenosis. The balloon is then inflated under a pressure and for a time sufficient to cause the blood vessel to be permanently dilated in region of the stenosis. This permanent dilation results from the force of the balloon breaking an internal elastic laminate boundary between an intima and a medial cell layer of the blood vessel. This permanent dilation caused by PTCA is a controlled injury having beneficial therapeutic effects. Other therapeutic injuries can be caused by interventional procedures other than PTCA.

The blood vessel frequently reacts to the disruption of these tissue layers (caused by PTCA or other intervention) by restenosing, sometimes resulting in reocclusion of the blood vessel. A significant factor in restenosis is the proliferation of smooth muscle cells in the medial cell layer of the blood vessel. Another factor in restenosis includes an acute thrombotic reaction which is associated with exposure of the medial cell layer to blood circulating in the vessel. Finally, elastic recoil in the blood vessel wall, which reduces or eliminates the permanency of the dilation, and remodeling of plaque in the stenosed region are also associated with restenosis.

Various attempts at solving the problem of restenosis after PTCA, or other vessel injuries, have been offered but none provide an overall acceptable solution. These prior attempts include using drugs to inhibit medial smooth cell proliferation or the delivery of ionizing radiation (e.g., Beta emitters, x-rays, gamma-rays) to neutralize the medial smooth cell layer and thereby prevent smooth cell proliferation. However, delivery of ionizing radiation is difficult to handle and poses a risk of exposure to health care providers. Various methods of applying heat to the vessel wall (e.g., conductive transfer via hot balloon, laser, infrared) have been presented to minimize restenosis. Examples of several of these approaches are disclosed in Weinberger U.S. Pat. No. 5,503,613, Abele et al. U.S. Pat. No. 5,496,311, Sterzer U.S. Pat. Nos. 4,924,863 and 5,098,429, Lennox U.S. Pat. No. 4,955,377, and Spears U.S. Pat. No. 5,092,841. However, none of these methods satisfactorily prevent restenosis after a PTCA treatment or other blood vessel injury. Although stents have also been used to open and maintain a blood vessel in a patent state, stents require permanent placement in the vessel.

SUMMARY OF THE INVENTION

A method of the present invention reduces restenosis of a stenotic region of a blood vessel by radiating microwave energy from a microwave antenna to kill a medial tissue layer of the blood vessel in the stenotic region. The radiation is applied during or after inflation of a dilatation balloon of a PTCA catheter to permanently dilate the stenotic region. Alternatively, the radiation is applied after another interventional procedure that therapeutically injuries a stenotic region of a blood vessel. Killing the medial cell layer with microwave radiation prevents smooth muscle cell proliferation in the stenotic region, which is believed to be a primary factor in restenosis. In addition, in instances when the radiation is applied during dilatation of the stenotic region, the dilatation balloon forms a seal against the inner wall surface of the blood vessel. This seal prevents blood in the vessel from contacting the stenotic region, thereby preventing the potentially triggering of medial layer smooth cell proliferation and/or an acute thrombotic reaction in the blood vessel, which is also associated with restenosis. In addition, preservation of the intima by thermal protection (i.e., cooling) via dilatation balloon further insulates the medial cell layer from exposure to agents which could trigger smooth muscle cell proliferation.

In one embodiment, the method of the present invention further includes circulating cooling fluid within cooling lumens of the catheter to cool the blood circulating in the blood vessel about a shaft of the catheter. This cooling action prevents the circulating blood from coagulating during the application of microwave radiation to the stenotic region of the blood vessel. The cooling fluid within the cooling lumens also conductively cools an inflation fluid within the dilatation balloon thereby permitting the balloon inflation fluid to cool an inner wall surface of the blood vessel in the stenotic region during the application of microwave radiation to the medial cell layer in the stenotic region. This cooling action further aids in preventing the thrombotic action from the coagulation of blood in the vessel and along the vessel wall, which is associated with restenosis.

Finally, in one embodiment, the catheter includes a perfusion means for directing the passage of blood from the vessel into and through the catheter and back into the blood vessel to maintain circulation of blood through the blood vessel during dilatation of the stenotic region.

The method and device of the present invention acts in at least three ways to prevent restenosis after a balloon dilatation angioplasty procedure (or other interventional procedure causing a therapeutic injury to the blood vessel) by neutralizing several factors associated with restenosis. First, application of microwave radiation kills the medial cell layer, which is associated with smooth muscle cell proliferation. Second, the method preferably excludes blood from the stenotic region until after the medial cell layer is destroyed since exposure of circulating blood to the medial cell layer is also associated with restenosis. Third, cooling action prevents coagulation of blood circulating in the blood vessel and prevents thrombotic action along the vessel wall in the stenotic region, both of which are associated with restenosis and other health risks. Fourth, cooling action protects the intima and also may prevent restenosis.

BRIEF DESCRIPTION OF THE DRAWINGS

FIG. 4 is a sectional view of the catheter of FIG. 1 as taken along lines 4—4.

FIG. 5 is a sectional view of the catheter of FIG. 1 as taken along lines 5—5.

FIG. 6 is an enlarged sectional view of the antenna of the catheter of the present invention.

FIG. 7 is a sectional view of a catheter of the present invention in use in a blood vessel.

FIG. 8 is a sectional view of FIG. 7 taken along lines 8—8.

FIG. 11 is a sectional view of an alternate embodiment of a catheter of the present invention.

DETAILED DESCRIPTION OF THE PREFERRED EMBODIMENTS

Figure 1:
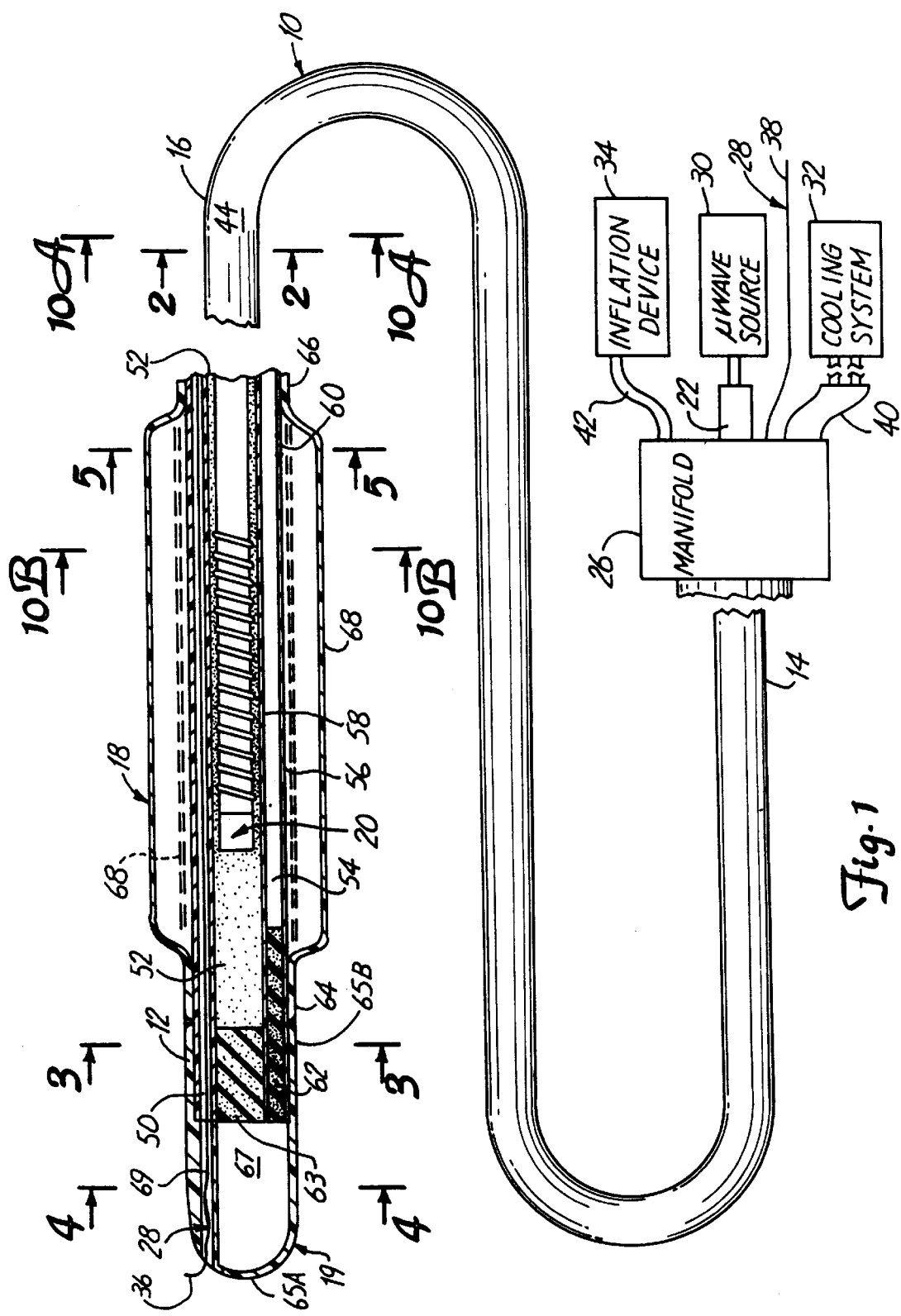
FIG. 1 is a sectional view of a catheter of the present invention with a proximal end and a distal end of the catheter enlarged for clarity.

Angioplasty catheter 10 of the present invention is illustrated generally in FIG. 1 and includes distal end 12, proximal end 14, and multi-lumen shaft 16. FIG. 1 shows a side view of catheter 10 including a sectional view of distal end 12 and a plan view of proximal end 14. Both distal end 12 and proximal end 14 are enlarged relative to catheter shaft 16 for illustrative purposes. Catheter 10 further includes dilatation balloon 18, atraumatic tip 19, microwave antenna 20, coaxial cable 22, and manifold 26. Catheter 10 is used with guide wire 28, microwave energy generator 30, cooling system 32, and inflation device 34. Guide wire 28 includes distal end 36 and proximal end 38.

Catheter 10 is used in a method of preventing restenosis in which antenna 20 and dilatation balloon 18 are placed across a stenosis in a blood vessel. The dilatation balloon 18 is used to permanently dilate the stenotic region according to well known angioplasty procedures while antenna 20 is used to apply microwave radiation to kill a medial cell layer of the blood vessel wall to prevent restenosis of the blood vessel. Dilatation balloon 18 also cools an inner wall surface of the blood vessel in the stenotic region conductively via the inflation fluid, which is either passively or actively cooled via shaft 16.

As shown in FIG. 1, manifold 26 of catheter 10 receives coaxial cable 22 (from microwave generating source 30), cooling system delivery tubing 40, guide wire 28, and inflation device connector 42 for alignment with corresponding lumens within shaft 16. Shaft 16 is an extruded multi-lumen, intravascular catheter shaft connected to manifold 26 at proximal shaft end 14. Manifold 26 and shaft 16 are preferably made of a suitable polymeric material known to those skilled in the art.

Shaft 16 also includes outer surface 44. In one preferred embodiment, shaft 16 includes a coating (e.g., TEFLON®) having a low coefficient of friction well known in the art forming outer surface 44 of shaft 16 to facilitate its advancement through a guide catheter positioned within the vascular system. Shaft 16 has an outer diameter of about 0.1 inches, suitable for insertion within a 10 French size guide catheter. Shaft 16 is long enough (e.g., 135 centimeters) and of a small enough diameter to permit insertion of distal shaft end 12 through the vascular system and into a coronary blood vessel. A proximal portion of shaft 16 can be augmented with additional design features well known to those skilled in the art to provide adequate steerability, size, pushability, tracking, and biocompatibility. In addition, the catheter polymer material forming shaft 16 can include a radiopaque filler material well known in the art (e.g., bismuth subcarbonate or barium sulfate) to facilitate visualization of catheter shaft 16 under fluoroscopy.

As shown in FIG. 1 adjacent catheter distal end 12, catheter shaft 16 further includes guide wire lumen 50, antenna lumen 52, balloon inflation lumen 54, outer wall 56 and inner wall 58. Outer wall 56 includes inflation port 60 while inflation lumen 54 includes plug 62 and antenna lumen 52 includes plug 63. Finally, dilatation balloon 18 includes distal waist 64, proximal waist 66, and expandable wall portion 68. Guide wire lumen 50 extends the full length of catheter shaft 16 and through atraumatic tip 19 and is sized to receive conventional guide wire 28. Inflation lumen 54 extends from the catheter proximal end 14 to a point adjacent catheter distal end 12 where lumen 54 is closed by plug 62.

Microwave antenna lumen 52 is aligned centrally relative to the longitudinal axis of shaft 16 along the length of shaft 16 and at its proximal end, antenna lumen 52 communicates with manifold 26. Antenna lumen 52 is adapted for receiving microwave antenna 20 to be permanently positioned within antenna lumen 52 near dilatation balloon 18 so that antenna 20 will be generally situated adjacent a stenosis when shaft 16 is properly positioned within a coronary blood vessel. Antenna 20 can be bonded within antenna lumen 52 by an adhesive and is carried at the distal-most end of coaxial cable 22. The proximal-most end of coaxial cable 22 is connected to microwave generating source 30. Microwave generating source 30 produces high frequency microwaves, preferably at about 915 MHz, although other frequencies such as about 2450 MHz can be used. When antenna 20 is energized by microwave generating source 30, antenna 20 emits electromagnetic energy which causes selective heating of a medial cell layer within a wall of a blood vessel.

Dilatation balloon 18 cooperates with multi-lumen shaft 16 and is secured about distal end 12 of catheter shaft 16. Distal waist 64 of balloon 18 is bonded to shaft exterior surface 44 at distal shaft end 12 while proximal waist 66 of balloon 18 is bonded to shaft outer surface 44 proximal to antenna 20. With dilatation balloon 18 secured in this manner, shaft outer surface 44 and expandable wall portion 68 define a chamber which can be inflated (as seen in FIG. 1) and deflated (shown in phantom in FIG. 1) by the selective introduction and removal of an inflation fluid within an interior of expandable wall portion 68 through port 60 of inflation lumen 54. Dilatation balloon 18 is provided so that when filled with an inflation fluid, dilatation balloon 18 expands to dilate a stenotic region of the coronary blood vessel.

Dilatation balloon 18 extends for a length adjacent distal shaft end 12 that is substantially less than the length of catheter shaft 16. For example, expandable wall portion 68 of dilatation balloon 18 preferably has a length of about 2 to 4 centimeters. Dilatation balloon 18 is a flexible tubular member formed of PET, cross-linked polyethylene or some other thermoplastic material known to those skilled in the art suitable for dilatation procedures.

Atraumatic tip 19 includes distal end 65A and proximal end 65B and has a hollow, flexible resilient body defining a chamber 67 located beyond the distal end 12 of catheter shaft 16. Tip proximal end 65B defines a waist that is adhesively secured on catheter outer surface 44 in an abutting relationship adjacent dilatation balloon distal waist 64. Finally, atraumatic tip 19 further includes a lumen 69 that acts as an extension of guide wire lumen 50 to permit the passage of guide wire 28 through tip 29.

Figure 2:
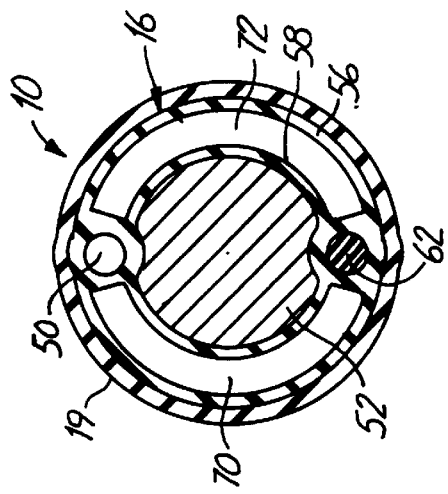
FIG. 2 is a sectional view of the catheter of FIG. 1 as taken along lines 2—2.

FIG. 2 is a sectional view of catheter shaft 16 proximal to dilatation balloon 18. As shown in FIG. 2, guide wire lumen 50, antenna lumen 52, and balloon inflation lumen 54 each preferably have a generally circular shaped transverse cross-section. Microwave antenna lumen 52 preferably has a generally circular shaped transverse cross-sectional area which is substantially larger than a transverse cross-sectional area of any other respective lumen of catheter shaft 16. Antenna lumen 58 preferably has a diameter of about 0.060 inches while guide wire lumen 50 preferably has a diameter of about 0.015 inches. Balloon inflation lumen 54 preferably has a diameter of about 0.012 inches.

In addition, as shown in FIG. 2, catheter shaft 16 further includes cooling lumens 70 and 72. Cooling fluid intake lumen 70 and exhaust lumen 72 extend from proximal shaft end 14 to distal shaft end 12 where lumens 70 and 72 terminate and where cooling fluid intake lumen 70 communicates with cooling exhaust lumen 72. Cooling fluid lumens 70 and 72 are defined by inner wall 58 and outer wall 56 and preferably have a generally arc shaped transverse cross-section configured to surround antenna lumen 52. Cooling lumens 70 and 72 preferably have a uniform radial thickness of about 0.010 inches. In combination, cooling lumens 70 and 72 substantially surround antenna lumen 52 about a substantial majority (about 85%) of a circumference of antenna lumen 52. Cooling lumens 70 and 72 surround antenna lumen 52, so that when filled with a cooling fluid, cooling lumens 70 and 72 cool the catheter shaft outer surface 44 and absorb heat from the artery surface, (which is created by the microwave energy) to protect blood immediately surrounding catheter shaft 16 within a blood vessel.

Figure 3:
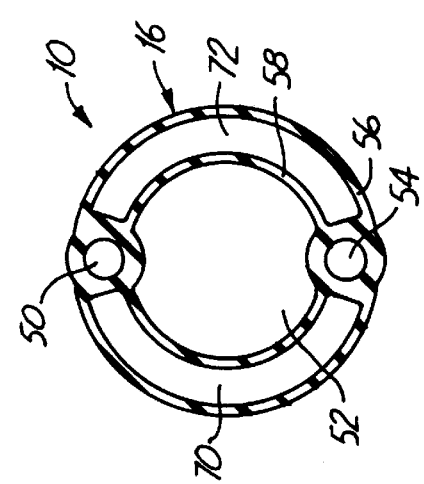
FIG. 3 is a sectional view of the catheter of FIG. 1 as taken along lines 3—3.

FIG. 3 is a sectional view of catheter shaft 16 distal to dilatation balloon 18 adjacent catheter distal end 12. As shown in FIG. 3, balloon inflation lumen 54 is sealed shut with plug 62 and antenna lumen 52 is sealed shut with plug 63. This arrangement adjacent catheter distal end 12 closes balloon inflation lumen 54 and antenna lumen 52 while cooling lumens 70 and 72 remain open within catheter shaft distal end 12 for communication with each other and guide wire lumen 50 remains open through utmost end of catheter shaft distal end 12.

FIG. 4 is a sectional view of atraumatic tip 19 distal to utmost catheter distal end 12. As shown in FIG. 4, tip 19 defines chamber 67 and guide wire lumen extension 69. Guide wire lumen extension 69 permits the passage of guide wire 28 through atraumatic tip 19. Chamber 67 provides a common area for communication between cooling lumens 70 and 72 distal to utmost catheter distal end 12 to facilitate circulation of cooling fluid from cooling intake lumen 70 into cooling exhaust lumen 72.

At catheter proximal end 14, cooling intake lumens 70 and cooling exhaust lumens 72 cooperate with cooling system 32 (via manifold 26 as shown in FIG. 1) to provide a selectively controlled flow of fluid through cooling lumens 70 and 72 during a treatment session. For example, in one embodiment, intake lumen 70 is supplied with deionized water from cooling system 32. Water from cooling system 32 is chilled to about 8° C. and pumped through cooling fluid intake lumen 70 toward distal shaft end 12. Under fluid pressure, water enters cooling fluid exhaust lumen 72 via chamber 67 of atraumatic tip 19 and returns to cooling system 32 through exhaust lumen 72 for re-chilling and re-circulation. Cooling system 32 is capable of circulating fluid at a high speed rate to maintain fluid with shaft 16 at a relative low temperature (e.g., 8° C.).

FIG. 5 is a sectional view of catheter shaft 16 and dilatation balloon 18. As shown in FIG. 5, expandable wall 68 of balloon 18 is arranged concentrically about catheter shaft 16 to surround catheter shaft outer surface 44 and cooling lumens 70 and 72. Balloon inflation lumen 54 communicates with an interior of dilatation balloon 18 via inflation port 60. Dilatation balloon 18 is inflated by inflation device 34 (FIG. 1) which selectively supplies inflation fluid to balloon 18 through lumen 54 under pressure sufficient to dilate a stenotic region of a blood vessel. Accordingly, selective inflation and deflation of dilatation balloon 18 permits the selective dilatation of a blood vessel to perform the well known PTCA procedure. As shown, expandable portion 68 preferably has a generally circular shaped transverse cross-section when inflated. Dilatation balloon 18 has a wall thickness of about 0.0005 to 0.005 inches, preferably having a thickness of 0.005 inches. When inflated, dilatation balloon 18 has a predetermined diameter selected in the range of about 2.5 to 6.5 millimeters. In addition, outer wall 56 defining cooling lumens 70 and 72 has a thickness and strength sufficient to maintain the arcuate shape of the cooling lumens 70 and 72 should pressure within the dilatation balloon exceed fluid pressures in the cooling lumens 70 and 72.

Unlike known methods, with the present invention cooling fluid passing through cooling lumens 70 and 72 passively cools (via conduction) inflation fluid within dilatation balloon 18 and inflation lumen 54. Passive cooling of the balloon inflation fluid permits the expandable wall 68 of the balloon 30 to cool an inner surface wall of a blood vessel when the dilatation balloon 18 presses against the vessel inner wall surface during dilatation of the vessel wall. Accordingly, the passive cooling provided by cooling fluid circulating in cooling lumens 70 and 72 effectively converts the balloon inflation fluid and dilatation balloon 18 into a cooling chamber to cool the surrounding blood vessel wall surface.

FIG. 6 illustrates in detail the microwave antenna 20 used in the present invention to radiate the medial cell layer of a stenotic region of a blood vessel wall. Antenna 20 is designed so that an outer diameter of antenna 20 is no greater than an outer diameter of coaxial cable 22, and so that antenna 20 is relatively short, e.g., about 2–3 centimeters. As previously described, microwave antenna 20 is positioned within microwave antenna lumen 52 and is surrounded by cooling lumens 70 and 72 and dilatation balloon 18.

FIG. 6 illustrates a sectional view of microwave antenna 20 along its length. Antenna 20 is positioned at the distal most end of shielded coaxial cable 22. Cable 22 is a standard miniature 30 AWG or 32 AWG coaxial cable and can be obtained from CoonerWire of Chatsworth, Calif. Coaxial cable 22 includes inner conductor 100, inner insulator 102, outer conductor 104, and outer insulator 106. Antenna 20 further includes transition portion 108, reduced diameter portion 110 of inner insulator 102, first tubular extension 112, second tubular extension 114, and annular collar 116. Antenna 20 also includes a flat wire coil 118, capacitor 120, solder 122, and end cap 124.

First tubular extension 112 encompasses outer conductor 104 and reduced diameter portion 110 of inner insulator 102. A proximal end of tubular extension 112 is positioned adjacent transition portion 108 of cable 22. Annular collar 116 also encompasses outer conductor 104 and reduced diameter portion 110 of inner insulator 102 and abuts a distal end of tubular extension 112. Annular collar 116 is a conductive material that is in electrical contact with outer conductor 104 and wire coil 118. Second tubular extension 114 also encompasses outer conductor 104 and reduced diameter portion 110 of inner insulator 102 with a proximal end of second tubular extension 114 abutting annular collar 116. A distal end of second tubular extension 114 has end cap 124 disposed therein.

Flat wire 118 forms a coil about tubular extensions 112 and 114. Capacitor 120 is secured about a distal end of inner conductor 100 and is further electrically connected to flat wire coil 118 by solder 122 extending through hole 126.

Reduced diameter portion 110 preferably has an outer diameter of about 0.05 inches. Tubular extensions 112 and 114 have lengths of 1 inches and 0.8 inches, respectively, and can have a thickness of about 0.005 inches. Reduced diameter portion 110 and tubular extensions 112 and 114 have outer diameters (or thicknesses) of a size so that when antenna 20 is fully constructed, antenna 20 has an outer diameter of about 0.060 inches or less.

Antenna 20 includes a first coil section 140 and a second coil section 142, both of which are of equal length. These two sections are created by the electrical connection of annular collar 116 with flat wire coil 118 at a midsection of flat wire coil 118. In one embodiment, first and second coil sections 140 and 142 are each comprised of five equally-spaced windings of flat wire coil 118 about tubular extensions 112 and 114, respectively. The combined length of first and second coil sections 140 and 142 provide an overall length of antenna 20 of about 2 centimeters. However, this overall length and the number of windings of the coil can be varied as needed to provide the desired length of antenna coil 118.

In one embodiment of the present invention, flat wire 118 is made of a flat ribbon of copper or silver and can be plated with a highly conductive material. The ribbon can be 0.02 inches wide and 0.006 inches thick. Flat wire 118 has a physical length of 4.5 inches, which when coiled provides a total length for first coil wire section 140 and second coil wire section 142 of 2 centimeters.

The location along coil 118 of an electrical connection between first coil section 140 and capacitor 120 corresponds to a tap point used for impedance matching. Specifically, a tap point is selected along coil 118 so that an impedance presented between the tap point and annular collar 116 (corresponding to the point of electrical connection between coil 118 and inner conductor 100) matches the characteristic impedance of coaxial cable 22. As shown in FIG. 6, in this embodiment, the tap point is located adjacent the end of first coil section 140 of coil 118. However, the tap point can be located nearer to annular collar 116 as necessary to obtain the required impedance match.

The impedance of either first coil section 140 or second coil section 142 also includes an inductive component which is eliminated by providing a series capacitance such as capacitor 120. Accordingly, tubular capacitor 120 serves to counteract a reactive component of antenna 34, thereby providing a fifty (50) Ohm resistive impedance match between coaxial cable 22, microwave generating source 30, and antenna 20.

Tubular capacitor 120 preferably has a value of about 2.7 pF and can be obtained from Coors Ceramics Co. of Golden, Colo. Capacitor 120 preferably is sized to fit over an inner conductor 100 and has a length of 0.125 inches, an outer diameter of about 0.045 inches, and an inner diameter of about 0.025 inches. Tubular capacitor 120 is substantially similar in design to a tubular capacitor described and shown in Rudie et al. U.S. Pat. No. 5,370,677, which is hereby incorporated by reference, and is mounted and connected to the inner conductor 100 and flat wire antenna coil 118 in a manner substantially similar to that described in Rudie et al. U.S. Pat. No. 5,370,677.

While the preferred dimensions for reduced diameter portion 110 have been identified above, the relatively smaller radial dimensions of reduced diameter portion 110 of inner insulator 102 could result in a characteristic impedance different than 50 Ohms. The characteristic impedance (Zo) can be calculated with the following equation:

$$Z_o = \frac{138}{\sqrt{\epsilon_r}} \log_{10}\left(\frac{D}{d}\right)$$

where $\epsilon_r$ is the relative dielectric constant of the inner insulator 102, D is the inner diameter of outer conductor 104, and d is the outer diameter of inner conductor 100. Accordingly, a characteristic impedance of 50 Ohms can be maintained with a reduced diameter portion 110 by adjusting the ratio of D/d (e.g., reducing d), by selecting an appropriate relative dielectric constant ($\epsilon_r$), or by adjusting both the ratio D/d and the relative dielectric constant ($\epsilon_r$). Alternatively, any resulting impedance mismatch resulting from the altered diameter of reduced diameter portion 110 of inner insulator 102 can be remedied by selecting an appropriate tap point location and a corresponding capacitor value for capacitor 120.

Finally, antenna 20 can include platinum or gold bands located adjacent either or both ends of the flat wire antenna coil 118 to facilitate positioning of antenna 20 and catheter 10 within the cardiovascular system since the gold bands will substantially improve visualization of antenna 20 under fluoroscopy.

Antenna 20 generally has a helical dipole construction similar to the helical dipole construction of a microwave antenna described and shown in Rudie et al., U.S. Pat. Nos. 5,300,099 and 5,370,677, which are hereby incorporated by reference. Accordingly, the helical dipole construction of antenna 20 of the present invention has an effective electrical length generally equal to one-half of the wave length of the radiation emitted in the surrounding medium, e.g., the catheter shaft and surrounding tissue. Because of the helical dipole construction of antenna 20, in accordance with Rudie U.S. Pat. Nos. 5,300,099 and 5,370,677, antenna 20 can have different physical lengths yet have the same effective electrical length to produce a consistent and predictable pattern of radiation.

In addition, the antenna illustrated and described in U.S. Pat. Nos. 5,300,099 and 5,370,677 can be used in catheter 10 (in place of the antenna of FIG. 6) when appropriately sized and is hereby incorporated by reference.

In use, catheter 10 is employed in a PTCA procedure within a stenosed blood vessel. FIGS. 7 and 8 show enlarged sectional views of a blood vessel 150 with catheter 10 properly positioned within blood vessel 150. Blood vessel 150 includes intima 152, internal elastic laminate 154, medial layer 156, adventitia 158, and stenotic region 160. Stenotic region 160 includes plaque and other deposits formed along intima 152 as is well known in the art. Accordingly, FIGS. 7 and 8 omit an illustration of the plaque for clarity sake in illustrating the catheter 10 and major vessel components.

In accordance with known angioplasty techniques using guide wire 28 and a guide catheter (not shown), catheter 10 is inserted into the guide catheter from outside the body at a remote location (e.g., femoral artery). The catheter 10 is advanced through the cardiovascular system until dilatation balloon 18 of catheter 10 is maneuvered across stenotic region 160 in its deflated state and is then inflated as shown to dilate stenotic region 160. In this position, the expandable wall 68 presses against intima 152 with sufficient pressure to seal off stenotic region 160 from blood circulating in blood vessel 150 and with sufficient pressure to break internal elastic laminate 154 to permanently dilate stenotic region 160 in accordance with well known angioplasty techniques.

With dilatation balloon 18 dilated fully, microwave antenna 20 is energized by microwave generating source 30 which causes antenna 20 to radiate microwaves at 902–928 MHz frequency. The microwave radiation is applied at a power (e.g. 25 watts) and for a time sufficient to cause the medial cell layer 156 to be heated inductively and to be substantially destroyed. The volume of tissue including the medial cell layer 156 is heated according to a time and temperature relationship which substantially destroys the medial cell layer 156. The period of time and power level applied are manipulated to achieve heating above 45° C. to a select depth sufficient to destroy the medial cell layer 156. A discussion on the time and temperature relationship for causing necrosis of tissues is presented in the literature known to those skilled in the art including, but not limited to: Henriques, Studies of Thermal Injury, V. The Predictability and Significance of Thermally Induced Rate Processes Leading To Irreversible Epidermal Injury, ARCHIVES OF PATHOLOGY, Volume 43, pp. 489–502 (1947) and related articles by Henriques; and Dickson et. al., Thermosensitivity of Neoplastic Tissues In Vivo, HYPERTHERMIA IN CANCER THERAPY, Chapter 5, including supporting articles cited therein.

At the same time that the microwave energy is applied to the medial cell layer, cooling fluid circulating within the cooling lumens 70 and 72 passively cools the balloon inflation fluid within dilatation balloon 18 to thereby cool intima 152 in stenotic region 160 (via balloon expandable wall portion 68) and prevent substantial damage to intima 152. In addition, cooling fluid in cooling lumens 70 and 72 cools the blood circulating within blood vessel 150 to prevent the blood from coagulating and prevent thrombotic activity from occurring on the intima 152 of vessel 150.

This heating pattern created by catheter 10 allows greater temperature elevation (caused by microwave energy) to be concentrated primarily at medial cell layer 156 within the blood vessel 150 while intima 152 is protected from necrosing temperatures (e.g., above 45° C.). After a select amount of microwave energy has been applied to the medial cell layer 156, the dilatation balloon 18 can be deflated and the microwave antenna 20 de-energized. Once the dilatation balloon 18 is deflated, the catheter 10 can be removed from blood vessel 150 proximally through the cardiovascular system as is well known in the art.

The catheter of the present invention permits the application of microwave energy in a blood vessel to ablate a medial cell layer of stenotic region of a blood vessel. This capability is achieved by a combination of features including, amongst others, an efficient dipole helical antenna design and a cooling system. The cooling system includes a pair of cooling lumens and a dilatation balloon. Inflation fluid within the dilatation balloon is passively cooled by cooling fluid circulating through the cooling lumens adjacent the dilatation balloon. This passively cooled balloon inflation fluid within dilatation balloon 18 cools intima 152 via thermal conduction (when microwave antenna 20 within antenna lumen 52 is energized) so that the temperature of intima 152 immediately adjacent balloon 18, and intima 152 just distal and proximal to balloon 18 will remain below a necrosing temperature as desired (e.g., below 45° C.).

This cooling system acts in cooperation with the microwave radiation emitted by antenna 20 to substantially reduce or prevent significant restenosis by achieving several effects simultaneously. First, during the PTCA the microwave radiation kills the medial cell layer of the blood vessel in the stenotic region to reduce smooth muscle cell proliferation associated with restenosis after the PTCA. Second, dilatation of the blood vessel in the stenotic region during the application of microwave radiation effectively blocks exposure of circulating blood to the damaged tissue being radiated until after the medial cell layer is killed. This sealing action impedes blood borne stimuli from stimulating a smooth muscle cell proliferation response or thrombotic/coagulative response (associated with restenosis) while the medial cell layer is exposed to circulating blood. Third, cooling both blood circulating in the blood vessel and intima 152 (via the cooling lumens and the dilatation balloon) prevents thrombotic and coagulative action in the blood.

Figure 9A:
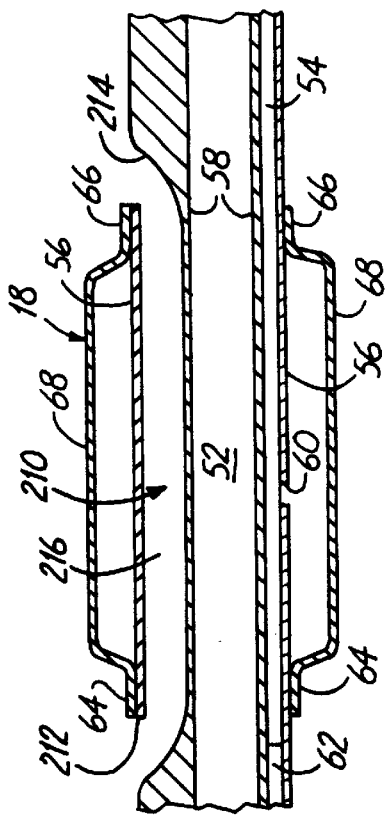
FIG. 9A is a sectional view of an alternate embodiment of the catheter of the present invention.
Figure 9B:
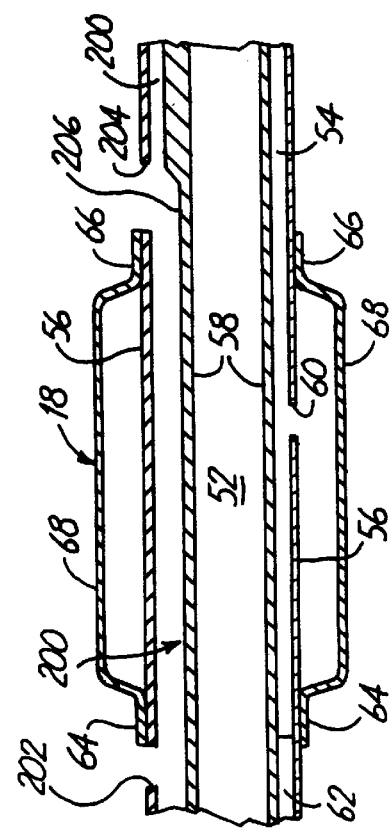
FIG. 9B is a sectional view of an alternate embodiment of the catheter of the present invention.

FIGS. 9A, 9B show alternative embodiments of catheter 10 of the present invention. In these embodiments, the structure of catheter 10 is substantially identical to the structure shown in FIGS. 1–8 except for replacing guide wire lumen 50 with guide wire lumen 200 (FIG. 9A) and guide wire lumen 210 (FIG. 9B), respectively. Guide wire lumen 200 is identical to guide wire lumen 50 except for an expanded region adjacent dilatation balloon 18 to permit perfusion. Guide wire lumen 200 includes distal port 202, proximal port 204, and expanded diameter portion 206. Guide wire lumen 200 of catheter 10 is used with guide wire 28 in a manner well known in as described in association with FIGS. 1–8.

Expanded portion 206 communicates with lumen 69 of atraumatic tip 19 to permit the passage of guide wire 28 and has a diameter sufficient to permit blood to pass therethrough with guide wire 28 also extending therethrough. During the dilatation of stenotic region 160 with balloon 18, blood circulating in blood vessel 150 is permitted to pass into proximal port 204 of guide wire lumen 200, through expanded portion 206, and out distal port 202 into the blood vessel 150. This expanded guide wire lumen 200 permits catheter 10 to perfuse blood past stenotic region 160 during a dilatation procedure, which would otherwise completely block the passage of blood through the stenotic region 160. Moreover, perfusion through guide wire lumen 200 can be accomplished without removing guide wire 28 from its position in blood vessel 150. This perfusion feature permits longer dilatation procedures, and more significantly, permits longer application of microwave radiation to the medial cell layer during dilatation to insure that the medical cell layer is substantially destroyed to ultimately reduce restenosis.

As shown in FIG. 9B, guide wire lumen 210 also replaces guide wire lumen 50 of catheter 10, which is completely eliminated from catheter shaft 16. Guide wire lumen 210 includes distal port 212, proximal port 214, and mid portion 216. Mid portion 216 has a diameter sufficient to permit perfusion of blood therethrough.

In use, guide wire 28 is placed in blood vessel 150 so that its distal end lies across stenotic region 160. The guide wire lumen 210 of catheter 10 is advanced onto guide wire 28 by guiding distal port 212 onto and over proximal end 38 of guide wire 28 until the guide wire proximal end 38 exits guide wire lumen proximal port 214. While maintaining the position of guide wire 28 within blood vessel 150, the catheter 10 is then advanced over guide wire 28 until dilatation balloon 18 is positioned across stenotic region 160. The combined dilatation and radiation steps are then performed as previously described in association with FIGS. 1–8. During the dilatation step, guide wire lumen 210 permits blood to pass from blood vessel 150 on the proximal side of stenosis 160 into proximal port 214, through portion 216, and out distal port 212 for further circulation in blood vessel 150 on a distal side of stenosis 160.

Figure 10B:
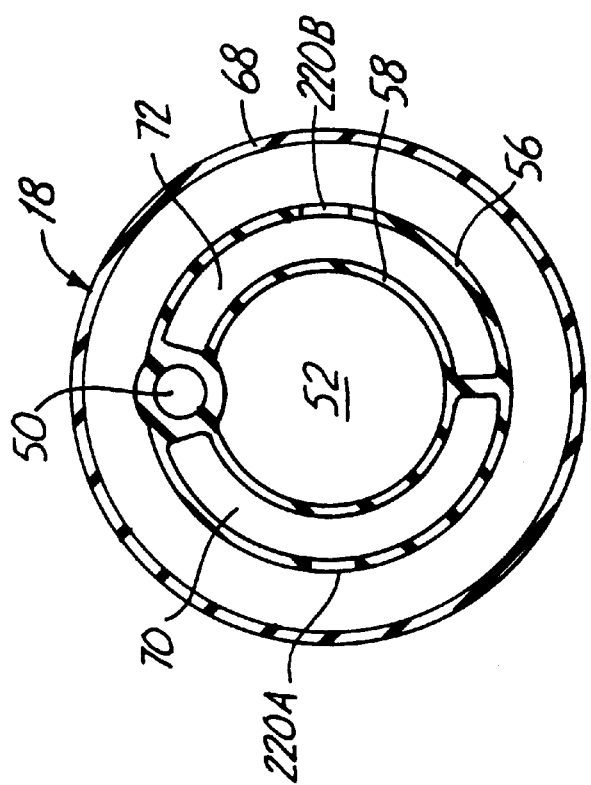
FIG. 10B is a sectional view of an alternate embodiment of the catheter of the present invention shown in FIG. 1 as taken along lines 10B—10B.
Figure 10A:
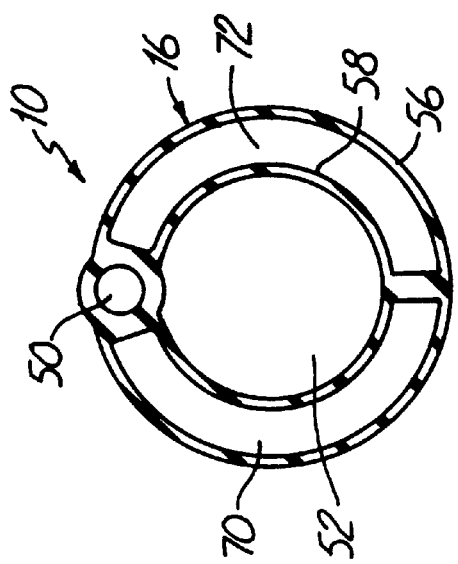
FIG. 10A is a sectional view of an alternate embodiment of the catheter of the present invention shown in FIG. 1 as taken along lines 10A—10A.

FIGS. 10A and 10B illustrate another alternate embodiment of catheter 10 of the present invention in which dilatation balloon 18 is inflated by cooling fluid that circulates through cooling lumens 70 and 72. FIG. 10A is a sectional view of alternate embodiment catheter shaft 16 proximal to dilatation balloon 18. As shown in FIG. 10A, catheter shaft 16 no longer includes balloon inflation lumen 54. FIG. 10B is a sectional view of this alternate embodiment catheter 10 at dilatation balloon 18. As shown, holes 220A and 220B are formed in outer wall 56. Hole 220A permits communication between cooling intake lumen 70 and an interior of dilatation balloon 18 while hole 220B permits communication between cooling exhaust lumen 72 and an interior of dilatation balloon 18. In use, cooling fluid passes out of cooling lumen 70 through hole 220A into the interior of dilatation balloon 18 where it circulates before passing out of the balloon interior into cooling exhaust lumen 72 through hole 220B. Cooling fluid is supplied under a pressure sufficient to inflate balloon to dilate the stenotic region 160 and at a rate of circulation sufficient to maintain the cool temperature of the fluid. In this embodiment, the cooling fluid both inflates dilatation balloon 18 and actively cools dilatation balloon 18 to place circulating cooling fluid immediately adjacent the blood vessel wall during the dilatation procedure. A cooling and pressurization system as discussed in association with FIGS. 11–14 can be used to supply adequate circulation and pressure to both inflate and cool dilatation balloon 18.

Another embodiment of a catheter of the present invention is illustrated in FIGS. 11–14 in which a dilatation balloon is inflated and actively cooled by a single cooled fluid supplied through the catheter shaft. Catheter 250 shown in FIG. 11 is used in a method of preventing restenosis like catheter 10 (shown in FIGS. 1–8). Catheter 250 includes distal end 252, proximal ends 254, and multi-lumen shaft 256. FIG. 11 shows a side view of catheter 250 including a sectional view of distal end 252 and a plan view of proximal end 254. Both distal end 252 and proximal end 254 are enlarged relative to shaft 256 of catheter 250 for illustrative purposes. Catheter 250 further includes dilatation balloon 258, atraumatic tip 257, microwave antenna 260, coaxial cable 262, and manifold 266. Catheter 250 is used with guide wire 268, microwave energy generator 270, and cooling and pressurization system 272. Guide wire 278 includes distal end 288 and proximal end 290.

Manifold 266 receives coaxial cable 262 (from microwave generating source 270), cooling and pressurization system inlet 284 and outlet 282, and guide wire 28 for alignment with corresponding lumens within shaft 256. Manifold 266 includes an inlet 283 for communicating with cooling and pressurization system outlet 282 and an outlet 285 for communicating with cooling and pressurization system inlet 284. Shaft 256 is an extruded multi-lumen, intravascular catheter shaft connected to manifold 266 of proximal shaft end 14. Multi-lumen shaft 256 has attributes and features similar to shaft 16 of catheter 10. Shaft 256 is made of a suitable polymeric material, has an outer surface 292, and is coated and sized appropriately to permit use in a cardiovascular system as previously disclosed with regard to shaft 16 of catheter 10.

As shown in FIG. 11 adjacent catheter distal end 252, catheter shaft 256 further includes guide wire lumen 300 and balloon inflation chamber 302. In addition, dilatation balloon 258 further includes distal end 304, proximal end 306, and expandable wall portion 308. Tip 257 includes distal end 309, body 310, and guide wire lumen extension 312, and proximal waist 311. Except for guide wire lumen 300, plug 313 and antenna terminal portion 314 define catheter shaft distal end 252 and define a distal end of balloon inflation chamber 302.

Guide wire lumen 300 extends the full length of catheter shaft 256 and tip 257 and is sized to receive conventional guide wire 268. Balloon inflation chamber 302 generally extends from a proximal end of plug 313 to a point adjacent balloon proximal waist 306. Chamber 302 has an outer wall defined by expandable wall 308, and inner wall defined by guide wire lumen 300 and antenna 260. As shown in FIG. 11 at the distal end 252 of catheter 250, antenna 260 and coaxial cable 262 are aligned centrally relative to the longitudinal axis of shaft 256 along the length of the distal end 252. Antenna 260 is fixed in this position with antenna terminal portion 312 being fixed in plug 313 at shaft distal end 252. Antenna 260 is arranged in shaft 256 relative to dilatation balloon 258 to be generally situated adjacent a stenosis when shaft 256 is properly positioned within a coronary blood vessel.

Antenna 260 is carried at the distal-most end of coaxial cable 262 while the proximal-most end of coaxial cable 262 is connected to microwave generating source 270. Microwave generating source 270 produces high frequency microwaves, preferably at about 915 MHz. When antenna 260 is energized by microwave generating source 270, antenna 260 emits electromagnetic energy which causes heating of tissue within a coronary blood vessel. Microwave antenna 260 includes microwave antenna 20 as previously described and as illustrated in FIG. 6, or alternatively includes a helical dipole microwave antenna described and shown in Rudie et al. U.S. Pat. Nos. 5,300,099 and 5,370,677, both of which are hereby incorporated by reference. In addition, antenna 20 is preferably coated with insulation (e.g., parylene) to insure insulation from cooling fluid circulating about antenna 260. Moreover, antenna 260 can be further insulated with polytetrafluoroethylene or another high temperature polymer material.

Like dilatation balloon 18 of catheter 10, dilatation balloon 258 cooperates with its multi-lumen shaft 256 and is secured about distal end 252 of catheter shaft 256 by bonding of distal waist 304 and proximal waist 306 to shaft outer surface 292. Dilatation balloon 258 can be inflated (as seen in FIG. 11) and deflated (shown in phantom in FIG. 11) by the selective introduction and removal of an inflation fluid within an interior of balloon inflation chamber 302 via multi-lumen catheter shaft 256. When filled with an inflation fluid under pressure, dilatation balloon 258 expands to permanently dilate a stenotic region of a coronary blood vessel.

As shown in FIG. 11 at catheter proximal end 254, cooling and pressurization system 272 includes heat exchanger 274, pump 276, reservoir 278, and pressurization device 280. Connectors 286 permit communication between the respective elements of the cooling and pressurization system 272. Cooling and pressurization system 272 is connected to manifold 266 for communication with corresponding lumens in multi-lumen shaft 256. System outlet 282 permits communication from heat exchanger 274 to cooling intake lumen 70 (via manifold 266) and system outlet 284 permits communication from cooling exhaust lumen 72 (via manifold 266) to reservoir 278. The cooling and pressurization system 272 is used in cooperation with multi-lumen shaft 256 to provide a liquid that is under pressure for inflating dilatation balloon 258 and that is chilled to provide cooling within dilatation balloon 258. The inlet 284 and outlet 282 of cooling and pressurization system 272 are also selectively controllable to cause a pressure differential between inlet 284 and outlet 282 to control the inflation and deflation of dilatation balloon 258 via cooling fluid intake and exhaust lumens 320 and 322 in catheter shaft 256.

Reservoir 278 contains the bulk of the fluid that circulates through multi-lumen shaft 256 and dilatation balloon 258. The reservoir includes a means for removing all air from the fluid circulating with catheter 250. Pressurization device 280 is provided to pressurize fluid within the cooling and pressurization system 272 to permit selective inflation of dilatation balloon 258. While pressurization device 280 is shown connected to reservoir 278, pressurization device 280 can be connected to pump 276 instead of reservoir 278. In addition, pressurization device could alternatively be connected directly to system inlet 284 and take the form of a conventional PTCA inflation device.

Pump 276 is capable of circulating fluid within system 272, catheter shaft 256 and dilatation balloon 258 at an operating pressure sufficient to inflate dilatation balloon 258 to perform dilatation angioplasty on a stenotic region of a coronary blood vessel. Pump 276 preferably is a peristaltic-type pump or other suitable pump known to those skilled in the art. Heat exchanger 274 is capable of transferring sufficient heat from the circulating inflation/coolant fluid to maintain a desired coolant temperature (e.g., 8° C.) as the coolant flows through the multi-lumen shaft 256 and dilatation balloon 258.

Figure 12:
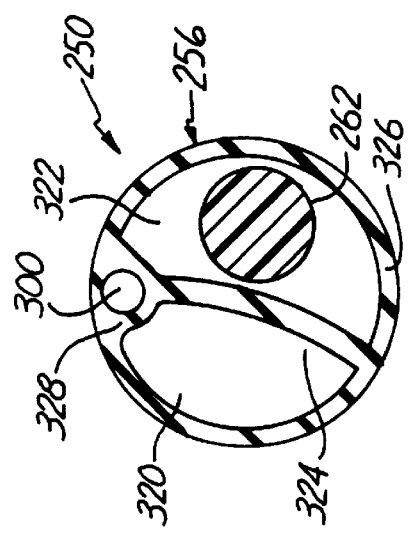
FIG. 12 is a sectional view of the catheter of FIG. 11 taken along lines 12—12.

FIG. 12 is a sectional view of catheter shaft 256 proximal to dilatation balloon 258. As shown in FIG. 12, guide wire lumen 300 preferably has a generally circular shaped transverse cross-section. In addition, catheter shaft 256 further includes cooling intake lumen 320 and cooling exhaust lumen 322, inner wall 324, outer wall 326, and guide wire lumen wall 328. Cooling fluid intake lumen 320 and exhaust lumen 322 extend from proximal shaft end 254 to distal shaft end 252 where lumens 320 and 322 terminate proximal to expandable wall portion 308 of dilatation balloon 258 (FIG. 11). Cooling lumens 320 and 322 are defined by inner wall 324 and outer wall 326 and preferably have a generally semi-circle shaped transverse cross-section with cooling lumen 322 configured to receive coaxial cable 262, which has a generally circular transverse cross section. When filled with cooling fluid from cooling and pressurization system 272, cooling lumens 320 and 322 provide cooling to protect blood circulating within a blood vessel immediately surrounding catheter shaft 256. Cooling fluid intake lumen 320 communicates with cooling exhaust lumen 322 near distal shaft end 252 within balloon inflation chamber 302 (defined by dilatation balloon 258).

Figure 14:
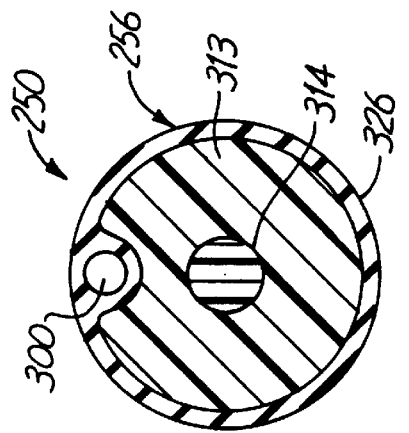
FIG. 14 is a sectional view of the catheter of FIG. 11 taken along lines 14—14.
Figure 13:
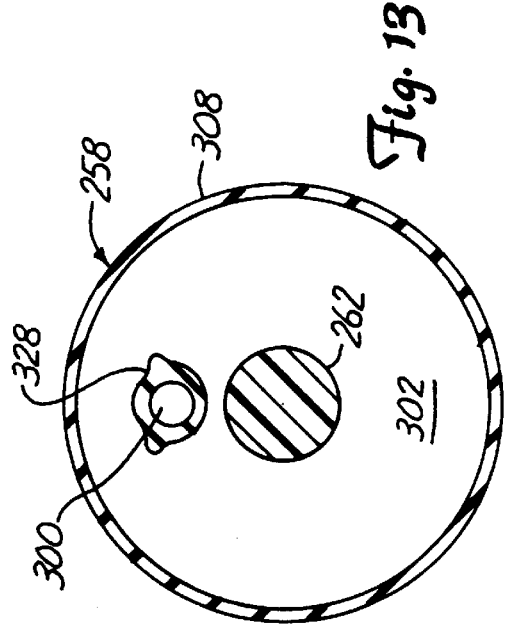
FIG. 13 is a sectional view of the catheter of FIG. 11 taken along lines 13—13.

FIG. 13 is a sectional view of catheter 250 at dilatation balloon 258. As shown in FIG. 13, expandable wall 308 of dilatation balloon 258 is arranged concentrically about coaxial cable 262 and guide wire lumen 300 (defined by guide wire lumen wall 328). However, outer wall 326 and inner wall 324 defining cooling lumens 320 and 322 has been removed so that guide wire lumen 300 and coaxial cable 262 (including antenna 260) are the only structures defining inner walls of balloon inflation chamber 302. Expandable wall 308 defines the outer wall of balloon inflation chamber 302. Guide wire lumen 300 is fixed in place at its distal end by its securement against catheter shaft outer wall 326 adjacent balloon distal waist 304, and is secured in place at its proximal end against outer wall 326, adjacent balloon proximal waist 306. Likewise, coaxial cable 262 (including antenna 260) is fixed within shaft 256 at the distal end by terminal portion 314 being lodged in plug 313 (FIG. 11). As shown in FIG. 14, antenna terminal portion 314 is fixed within plug 313 which completely fills and blocks an interior of catheter shaft 256 except for guide wire lumen 300 which extends the full length of catheter shaft 256. As shown in FIG. 12, the proximal portion of coaxial cable 262 (proximal to antenna 260) floats freely within lumen 322.

This arrangement permits cooling fluid to freely circulate in inflation chamber 302 defined by dilatation balloon 258. Cooling fluid cooled and supplied under pressure from cooling and pressurization system 272 enters chamber 302 from cooling intake lumen 320, and after circulating in chamber 302, exits into cooling exhaust lumen 322. Cooling fluid is supplied under a pressure sufficient to permanently dilate a stenotic region of a blood vessel upon inflation of dilatation balloon 258.

Catheter 250 is used in a method of preventing restenosis similar to that described for catheter 10 with regard to FIGS. 1–8. However, with catheter 250, cooling lumens 320 and 322 communicate directly with balloon inflation chamber 302. Fluid circulating within multi-lumen catheter shaft 256 (for cooling blood about catheter shaft outer surface 292) also circulates directly within dilatation balloon wall 308 and is used to both cool dilatation balloon wall 308 and to inflate dilatation balloon wall 308 in a manner sufficient to permanently dilate a stenotic region of a coronary blood vessel. The fluid also circulates under a pressure sufficient to effect permanent dilation of a stenotic region of any coronary blood vessel by virtue of pressurization device 280 of the cooling and pressurization system 272 while heat exchanger 274 acts to insure that fluid circulating within dilatation balloon 258 is at a temperature sufficient to cool intima 152 to protect intima from heat damage from energy radiated by microwave antenna 260.

As in the method described for catheter 10, catheter 250 is inserted and advanced in the cardiovascular system until the dilatation balloon 258 (in its deflated state) is placed across stenotic region 160 of blood vessel 150. Activation of cooling and pressurization system 272 causes circulation of cooling fluid through cooling lumens 320 and 322 to cool catheter shaft 256 and dilatation balloon 258 while simultaneously causing expandable wall 308 to expand outwardly and dilate the stenotic region. With the dilatation balloon 258 inflated by the circulating cooling and inflation fluid, microwave antenna 260 is activated to radiate microwave radiation into the blood vessel wall 150 to kill medial cell layer 156 while cooling/inflation fluid within dilatation balloon 258 protects intima 152. After a select amount of microwave energy has been applied to the medial cell layer 156 with microwave antenna 260, dilatation balloon 258 can be deflated and the microwave antenna 260 de-energized. Once the dilatation balloon 258 is deflated, the catheter 250 can be removed from blood vessel 150 proximally through the cardiovascular system.

As described with respect to catheter 10, a method using catheter 250 prevents restenosis of a stenotic region 160 of a blood vessel 150 by radiating microwave energy from microwave antenna 260 to kill medial cell layer 156 in the stenotic region 160. Radiation is applied during inflation of dilatation balloon 258, which permanently dilates the stenotic region. Killing the medial cell layer 156 prevents smooth muscle cell proliferation, which is believed to be a primary factor in restenosis. In addition, the expandable wall 308 of dilatation balloon 258 forms a seal against an inner wall surface of blood vessel 150 to exclude blood in vessel 150 from contacting the stenotic region 160 during the dilatation procedure. This sealing action prevents a potential triggering of medial smooth cell proliferation, inflammatory response or thrombotic action in the blood vessels associated with restenosis. Fluid circulating within cooling lumens 320 and 322 in catheter shaft 256 cools blood circulating within blood vessel 150 to prevent the blood from coagulating during the application of radiation to stenotic region 160. The cooling fluid which is also used to inflate dilatation balloon 258, cools an inner surface wall of blood vessel in a stenotic region conductively via dilatation balloon expandable wall 308.

Finally, the alternative embodiment for catheter 10 shown in FIGS. 9A and 9B (which includes expanded guide wire lumen 200 and 210, respectively) to permit perfusion of blood during the dilatation and radiation procedure, can be implemented in catheter 250 by similarly providing an expanded guide wire lumen in the region of dilatation balloon 258.

Accordingly, the method of the present invention using catheter 10 or catheter 250 acts in at least three ways to prevent restenosis after a balloon dilatation angioplasty procedure by neutralizing several factors associated with restenosis. First, application of microwave radiation kills the medial cell layer, which is associated with smooth muscle cell proliferation. Second, the method preferably excludes blood from the stenotic region until after the medial cell layer is destroyed since exposure of circulating blood to the medial cell layers is also associated with restenosis. Third, cooling action prevents coagulation of blood circulating in the blood vessel and prevents thrombotic action along the vessel wall in the stenotic region, both of which are associated with restenosis and other health risks.

While catheter 10 and catheter 250 have been described for use as a primary angioplasty PTCA dilatation catheter for permanently dilating a stenotic region along with applying radiation to kill a medial cell layer of a blood vessel to prevent restenosis, catheter 10 and catheter 250 can be used secondarily after a PTCA procedure has already been performed to permanently dilate a stenotic region of a blood vessel. To do so, the conventional PTCA procedure is performed using a conventional angioplasty dilatation balloon catheter. After that procedure, the dilatation balloon catheter is removed and catheter 10 or catheter 250 of the present invention is inserted and advanced until dilatation balloon 18 or dilatation balloon 258 lies across the stenotic region. The respective dilatation balloon (18, 258) of catheters 10 and 250, respectively, is then inflated sufficiently to establish wall contact with blood vessel 150 for creating a seal against intima 152 of blood vessel 150 to exclude blood circulating within blood vessel 150 from being further exposed to disruption of the inner wall surface of blood vessel 150 (including possible exposure to medial cell layer 156). With the dilatation balloon 18 or 258 expanded to provide a seal against intima 152, radiation is applied with the microwave antenna (20 or 260) to kill the medial cell layer of the stenotic region of the blood vessel. After radiation has been applied at sufficient power, length of time, and frequency, to substantially destroy the medial cell layer according to known time and temperature relationships for necrosing tissue, catheter 10 and catheter 250 can be removed as previously described.

However, the method of preventing restenosis with catheter 10 or catheter 250 in which catheter 10 or catheter 250 is used as a primary PTCA catheter for performing the dilatation step is preferred since the radiation step occurs simultaneously with the dilatation step. This excludes blood from the stenotic region until after the medial cell layer has been killed by radiation from the microwave antenna. This relationship may be important since it is believed that exposure of circulating blood to a medial cell layer may be strongly associated with smooth muscle cell proliferation and the accompanying restenosis.

Although the present invention has been described with reference to preferred embodiments, workers skilled in the art will recognize that changes may be made in form and detail without departing from the spirit and scope of the invention.

What is claimed is:

1. A method of preventing restenosis of a blood vessel comprising:

inserting and advancing a catheter through a cardiovascular system until a distal portion of the catheter extends across a stenotic region within the blood vessel of the system;

forcing contact between the stenotic region and a dilatation balloon located in the distal portion of the catheter;

cooling the inner wall surface of the blood vessel in the stenotic region with a first fluid circulating within the dilatation balloon; and heating a portion of the blood vessel in the stenotic region with microwave energy from a microwave antenna within the distal portion of the catheter at a temperature above about 45° C. for a period of time sufficient to substantially destroy a portion of the blood vessel in the stenotic region while cooling the inner wall surface of the blood vessel with the first fluid circulating within the dilatation balloon.

2. The method of claim 1 wherein the portion of the blood vessel being heated and substantially destroyed are smooth muscle cells of a medial cell layer of the blood vessel.

3. The method of claim 1 wherein the contacting step further comprises dilating the stenotic region with the dilatation balloon and further comprising:

performing the heating step and the cooling step during the dilating step, wherein the dilating step further includes:

inflating the dilatation balloon with the first fluid for a time and under a pressure sufficient to permanently dilate the stenotic region and sufficient to form a seal between the dilatation balloon and the inner wall surface of the blood vessel in the stenotic region.

4. The method of claim 1 wherein the step of cooling circulating the first fluid through a pair of cooling lumens located within the catheter in direct communication with the dilatation balloon, so the the first fluid circulates through both the cooling lumens and the dilatation balloon.

5. The method of claim 1 wherein the step of cooling further comprises circulating a second fluid within a pair of cooling lumens located within the catheter, wherein the first fluid within the dilatation balloon is cooled conductively through a wall of the cooling lumens by the second fluid circulating within the cooling lumens.

6. The method of claim 1 and further comprising:
   directing blood circulating in the blood vessel to pass through a perfusion lumen within the catheter located across the stenotic region during the dilating step to maintain circulation of blood within the blood vessel.

7. A method of preventing restenosis of a blood vessel comprising:
   inserting into a blood vessel of a cardiovascular system a catheter including an expandable dilatation balloon, a microwave antenna, and a pair of cooling lumens configured and arranged between the antenna and the dilatation balloon so that cooling fluid passing through the cooling lumen conductively cools an inflation fluid within the dilatation balloon;
   advancing the catheter within the blood vessel to locate the microwave antenna, the dilatation balloon, and a distal portion of the cooling lumens across a stenotic region of the blood vessel;
   inflating the dilatation balloon for a time and under a pressure sufficient to dilate the stenotic region and sufficient to force contact of an outer surface of the dilatation balloon against an inner wall surface of the blood vessel in the stenotic region to reduce contact between the blood in the blood vessel and the stenotic region;
   cooling blood circulating within the blood vessel and cooling the inner wall surface of the blood vessel in the stenotic region with the inflation fluid in the dilatation balloon; and
   heating a portion of the blood vessel with energy from the microwave antenna at a temperature above 45° C. for a time sufficient to substantially kill a portion of the blood vessel while dilating the stenotic region with the dilatation balloon, cooling blood circulating within the blood vessel cooling the inner wall surface of the blood vessel in the stenotic region with the inflation fluid in the dilatation balloon.

8. An angioplasty catheter for preventing restenosis of a blood vessel comprising:
   a catheter shaft having a distal end, a proximal end, and a plurality of lumens extending therebetween including:
      an antenna lumen;
      a guide wire lumen;
      an inflation lumen; and
      a pair of cooling lumens substantially surrounding the antenna lumen and in communication with each other adjacent the distal end of the shaft to permit circulation of cooling fluid through the cooling lumens;
   a microwave antenna located within the antenna lumen, the microwave antenna having a length and being operable to emit microwave radiation in a treatment region having a treatment length along the length of the microwave antenna; and
   a dilatation balloon inflatable to dilate the blood vessel, the dilatation balloon being in communication with the inflation lumen and arranged to at least partially surround the cooling lumens and the microwave antenna along the entire treatment length so that cooling fluid passing through the cooling lumens adjacent the dilatation balloon passively cools an inflation fluid within the dilatation balloon to cool an inner wall surface of the blood vessel around the microwave antenna.

9. The catheter of claim 8 and further comprising:
   a tip secured onto the distal end of the catheter shaft distal to the dilatation balloon, the tip having a guide wire extension lumen in communication with the guide wire lumen and defining a chamber in communication with each of the cooling lumens to permit communication between the cooling lumens.

10. The catheter of claim 9 and further comprising:
    a perfusion passageway having a distal port, a proximal port and a mid portion, the distal port and proximal ports being formed in an outer surface of the catheter shaft, the distal port being located distal to the dilatation balloon and the proximal port being located proximal to the dilatation balloon, wherein the mid portion extends between the distal and proximal ports coextensive with the dilatation balloon and is defined by an expanded diameter portion of the guide wire lumen.

11. An angioplasty catheter for preventing restenosis of a blood vessel comprising:
    a catheter shaft having a distal end, a proximal end, and a plurality of lumens extending therebetween including:
       an antenna lumen;
       an inflation lumen; and
       a pair of cooling lumens substantially surrounding the antenna lumen and in communication with each other adjacent the distal end of the shaft to permit circulation of cooling fluid through the cooling lumens;
    a microwave antenna located within the antenna lumen, the microwave antenna having a length and being operable to emit microwave radiation in a treatment region having a treatment length along the length of the microwave antenna;
    a dilatation balloon inflatable to dilate the blood vessel, the dilatation balloon being in communication with the inflation lumen and arranged to at least partially surround the cooling lumens and the microwave antenna along the entire treatment length so that cooling fluid passing through the cooling lumens adjacent the dilatation balloon passively cools an inflation fluid within the dilatation balloon to cool an inner wall surface of the blood vessel around the microwave antenna; and
    a guide wire and perfusion lumen extending within the shaft coextensive with a length of the dilatation balloon and having a distal port and a proximal port in an outer surface of the catheter shaft, the distal port being located distal to the dilatation balloon and the proximal port being located proximal to the dilatation balloon, the guide wire and perfusion lumen having a diameter sufficient to permit passage of a guide wire and the circulation of blood therethrough.

12. An angioplasty catheter for preventing restenosis of a blood vessel comprising:
    a catheter shaft having a distal end, a proximal end, and a plurality of lumens extending therebetween including:
       an antenna lumen;
       a guide wire lumen; and
       a pair of cooling lumens substantially surrounding the antenna lumen and being in communication adjacent the distal end of the catheter to permit circulation of cooling fluid through the cooling lumens;
    a microwave antenna located within the antenna lumen, the microwave antenna having a length and being operable to emit microwave radiation in a treatment region having a treatment length along the length of the microwave antenna;

a dilatation balloon inflatable to dilate the blood vessel, the dilatation balloon at least partially surrounding, and being in communication with, the cooling lumens so that the fluid passing through the cooling lumens inflates and cools the dilatation balloon, the inflatable dilatation balloon being arranged to at least partially surround the microwave antenna along the entire treatment length to cool an inner wall surface of the blood vessel around the microwave antenna.

13. An angioplasty catheter for preventing restenosis of a blood vessel comprising:

a catheter shaft having a distal end, a proximal end, and a plurality of lumens extending therebetween and including:
  a guide wire lumen; and
  a pair of cooling lumens including a cooling intake lumen and a cooling exhaust lumen;

a microwave antenna located within one of the cooling lumens, the microwave antenna having a length and being operable to emit microwave radiation in a treatment region having a treatment length along the length of the microwave antenna;

a dilatation balloon inflatable to dilate the blood vessel, the dilatation balloon being in communication with the cooling lumens and at least partially surrounding the cooling lumens and the microwave antenna along the entire treatment length; and wherein the cooling lumens are in communication with each other at a distal end of the catheter within the dilatation balloon so that a fluid passing through the cooling lumens circulates within the dilatation balloon to cool an inner wall surface of the blood vessel around the microwave antenna.

14. The catheter of claim 13 wherein each of the cooling lumens has a semi-circular shaped transverse cross-section the terminates adjacent the catheter distal end within an interior of the dilatation balloon.

15. The catheter of claim 14 and further comprising a cooling and pressurization system including:
  a heat exchanger;
  a pump;
  a reservoir;
  a pressurization device;
  wherein the heat exchanger, pump, reservoir and pressurization device are in communication in series and wherein the heat exchanger is in communication with the cooling intake lumen and the reservoir is in communication with the cooling exhaust lumen.

16. A method of preventing restenosis of blood vessel comprising:

inserting and advancing a catheter through a cardiovascular system until a distal portion of the catheter extends across a stenotic region within the blood vessel of the system;

forcing contact of a dilatation balloon located in the distal portion of the catheter against the stenotic region; and heating a medial tissue layer of the blood vessel in the stenotic region with microwave energy from a microwave antenna within the distal portion of the catheter at a temperature above about 45° C. for a period of time sufficient to substantially destroy smooth muscle cells in the medial tissue layer of the stenotic region while maintaining contact between the dilatation balloon and the stenotic region and while cooling the inner wall surface of the blood vessel in the stenotic region with a first fluid circulating within the dilatation balloon.

* * * * *